(12) United States Patent
Zeijlstra et al.

(10) Patent No.: US 9,775,961 B2
(45) Date of Patent: Oct. 3, 2017

(54) PATIENT INTERFACE

(71) Applicant: KONINKLIJKE PHILIPS N.V., Eindhoven (NL)

(72) Inventors: Harmina Christina Zeijlstra, Breda (NL); Mart Kornelis-Jan Te Velde, Helmond (NL); Sander Theodoor Pastoor, Ultrecht (NL); Richard Johannus Maria Van De Ven, Noord Brabant (NL)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 352 days.

(21) Appl. No.: 14/413,434

(22) PCT Filed: Jun. 28, 2013

(86) PCT No.: PCT/IB2013/055326
§ 371 (c)(1),
(2) Date: Jan. 8, 2015

(87) PCT Pub. No.: WO2014/009838
PCT Pub. Date: Jan. 16, 2014

(65) Prior Publication Data
US 2015/0151069 A1    Jun. 4, 2015

Related U.S. Application Data

(60) Provisional application No. 61/670,240, filed on Jul. 11, 2012.

(51) Int. Cl.
*A61M 16/06* (2006.01)
*A61M 16/08* (2006.01)

(52) U.S. Cl.
CPC ........ *A61M 16/0644* (2014.02); *A61M 16/06* (2013.01); *A61M 16/0622* (2014.02);
(Continued)

(58) Field of Classification Search
CPC ................................. A61M 16/0633–16/0655
See application file for complete search history.

(56) References Cited

U.S. PATENT DOCUMENTS

2007/0175480 A1* 8/2007 Gradon ............. A61M 16/0638
128/207.11
2008/0276937 A1   11/2008 Davidson
(Continued)

FOREIGN PATENT DOCUMENTS

DE    102008061007 A1    6/2009
EP        1205205 A2    5/2002
(Continued)

*Primary Examiner* — Valerie L Woodward
(74) *Attorney, Agent, or Firm* — Michael W. Haas

(57) ABSTRACT

The invention provides a patient interface (10) comprising a patient interface element (12, 14, 15) for delivering a breathing gas to a user and a forehead support (30). One of the forehead support and the patient interface element comprises a shaft (60) and the other comprises a hollow tube (62) in which the shaft is received, with the shaft slidable within the tube to permit adjustment of the position of the forehead support relative to the patient interface element. One of the shaft and hollow tube are elastically deformable between a deformed configuration in which the shaft can be slid within the tube and a released configuration in which the sliding of the shaft within the tube is blocked.

7 Claims, 4 Drawing Sheets

(a)

(b)  (c)

(52) U.S. Cl.
CPC .... *A61M 16/0655* (2014.02); *A61M 16/0683* (2013.01); *A61M 16/0816* (2013.01)

(56) References Cited

U.S. PATENT DOCUMENTS

| | | | | |
|---|---|---|---|---|
| 2008/0314390 A1* | 12/2008 | Kwok | ............... | A61M 16/0683 128/207.11 |
| 2010/0000542 A1* | 1/2010 | Chu | ............... | A61M 16/06 128/206.21 |
| 2011/0094516 A1* | 4/2011 | Chang | ............... | A61M 16/06 128/206.28 |
| 2012/0111333 A1* | 5/2012 | Eifler | ............... | A61M 16/0683 128/205.25 |
| 2012/0266873 A1* | 10/2012 | Lalonde | ............... | A61M 16/0057 128/201.13 |

FOREIGN PATENT DOCUMENTS

| | | |
|---|---|---|
| EP | 1900389 A2 | 3/2008 |
| WO | WO2004021960 A2 | 3/2004 |
| WO | WO2009055549 A2 | 4/2009 |
| WO | WO2010133218 A2 | 11/2010 |

\* cited by examiner

PATIENT INTERFACE

CROSS-REFERENCE TO RELATED APPLICATIONS

This patent application claims the priority benefit under 35 U.S.C. §371 of international patent application no. PCT/IB2013/055326, filed Jun. 28, 2013, which claims the priority benefit under 35 U.S.C. §119(e) of U.S. Provisional Application No. 61/670,240 filed on Jul. 11, 2012, the contents of which are herein incorporated by reference.

FIELD OF THE INVENTION

The present invention relates to patient interfaces for transporting a gas to and/or from an airway of a user.

BACKGROUND OF THE INVENTION

There are numerous situations where it is necessary or desirable to deliver a flow of breathing gas non-invasively to the airway of a patient, i.e. without inserting a tube into the airway of the patient or surgically inserting a tracheal tube in their oesophagus. For example, it is known to ventilate a patient using a technique known as non-invasive ventilation. It is also known to deliver continuous positive airway pressure (CPAP) or variable airway pressure, which varies with the patient's respiratory cycle, to treat a medical disorder, such as sleep apnoea syndrome, in particular, obstructive sleep apnoea (OSA).

Non-invasive ventilation and pressure support therapies involve the placement of a patient interface element comprising a mask component on the face of a patient. The mask component may be, without limitation, a nasal mask that covers the patient's nose, a nasal pillow/cushion having nasal prongs that are received within the patient's nostrils, a nasal/oral mask that covers the nose and mouth, or a full face mask that covers the patient's face. The patient interface element interfaces between the ventilator or pressure support device and the airway of the patient, so that a flow of breathing gas can be delivered from the pressure/flow generating device to the airway of the patient.

Such elements are typically maintained on the face of a patient by headgear having one or more straps adapted to fit over/around the patient's head.

FIG. 1 shows a typical system to provide respiratory therapy to a patient. This system will be referred to in the description and claims as a "patient interface assembly".

The assembly 2 includes a pressure generating device 4, a delivery conduit 16 coupled to an elbow connector 18, and a patient interface 10. The pressure generating device 4 is structured to generate a flow of breathing gas and may include, without limitation, ventilators, constant pressure support devices (such as a continuous positive airway pressure device, or CPAP device), variable pressure devices, and auto-titration pressure support devices.

Delivery conduit 16 communicates the flow of breathing gas from pressure generating device 4 to patient interface 10 through the elbow connector 18. The delivery conduit 16, elbow connector 18 and patient interface device 10 are often collectively referred to as a patient circuit.

The patient interface 10 includes a patient interface element which is a mask 12 in the form of a shell 15 and cushion 14, which in the exemplary embodiment is a nasal and oral mask. However, any type of mask, such as a nasal-only mask, a nasal pillow/cushion or a full face mask, which facilitates the delivery of the flow of breathing gas to the airway of a patient, may be used as mask. The cushion 14 is made of a soft, flexible material, such as, without limitation, silicone, an appropriately soft thermoplastic elastomer, a closed cell foam, or any combination of such materials.

An opening in the shell 15, to which elbow connector 18 is coupled, allows the flow of breathing gas from pressure generating device 4 to be communicated to an interior space defined by the shell 15 and cushion 14, and then to the airway of a patient.

The patient interface assembly also includes a headgear component 19, which in the illustrated embodiment is a two-point headgear. Headgear component 19 includes a first and a second strap 20, each of which is structured to be positioned on the side of the face of the patient above the patient's ear.

Headgear component 19 further includes a first and a second mask attachment element 22 to couple the end of one of the straps 20 to the respective side of mask 12.

A problem with this type of assembly is that the headgear force vectors necessary to achieve a robust and stable seal against the face of the patient can cut a straight line near the corners of a patient's eyes, which can be uncomfortable and distracting.

In order to avoid this, it is well known to include as part of the patient interface a forehead support to spread the required forces over a larger area. In this way, an additional cushion support on the forehead balances the forces put by the mask around the nose or nose and mouth.

All faces are different to each other. When using a patient interface assembly which has a forehead support, this forehead support should be adjustable for personal fit. The offset between facial plane and the forehead support can differ in the range of 30 mm.

An example of known adjustment arrangement uses a rotating mechanism, controlled by a rotary knob. This mechanism results in an increase or decrease of the offset between the facial plane and the forehead support. The user has to rotate the knob to get the right offset and the right fit.

From an ergonomics perspective, rotating a knob is not the most convenient way to implement adjustment. The number of elements and required accuracy is costly and the assembly can be noise due to play between components.

SUMMARY OF THE INVENTION

According to the invention, there is provided a patient interface as claimed in claim 1.

In one aspect, the invention provides a patient interface comprising:
 a patient interface element for delivering a breathing gas to a user; and
 a forehead support coupled to the patient interface element;
 wherein one of the forehead support and the patient interface element comprises a shaft and the other of the forehead support and the patient interface element comprises a hollow tube in which the shaft is received, with the shaft slidable within the tube to permit adjustment of the position of the forehead support relative to the patient interface,
 wherein one of the shaft and hollow tube is elastically deformable between a deformed configuration in which the shaft can be slid within the tube and a released configuration in which the sliding of the shaft within the tube is blocked.

This arrangement enables adjustment of the forehead support position by a linear sliding. This enables the desired position to be reached quickly and easily. For example the forehead support can simply be pushed from a retracted position to a position in which it contacts the forehead, and is then locked in place. The locking is achieved by releasing the elastic member.

In one example, the shaft is threaded, and the hollow tube is threaded, and the threads engage in the released configuration, and wherein the tube is elastically deformable between an oval shape in the released configuration and a circular shape in the deformed configuration with clearance around the shaft.

In this way, the hollow tube can comprise an oval nut. The oval nut can make enough contact with the shaft to enable fine tuning of the position with rotational adjustment, but large rapid changes in position can be made by disengaging the nut from the shaft so that they can be slid relative to each other.

The shaft is for example coupled to the forehead support and the hollow tube is coupled to the patient interface element.

In another example, the shaft is elastically stretchable in its axial direction, and the hollow tube has an internal surface which grips the shaft when it is in the unstretched configuration. Again, linear adjustment can be made quickly and easily, for example by pulling on the shaft (or a handle attached to the shaft) to stretch the shaft and thus make it thinner. The forehead support can then be moved relative to the patient interface by sliding, and simple release of the shaft causes it to engage with the tube and be locked in position.

The shaft can again be coupled to the forehead support and the hollow tube is then coupled to the patient interface element.

A strap arrangement can be provided for holding the mask and forehead support against the head of the patient, to form a patient interface assembly.

BRIEF DESCRIPTION OF THE DRAWINGS

Examples of the invention will now be described in detail with reference to the accompanying drawings, in which.

DETAILED DESCRIPTION OF THE EMBODIMENTS

The invention provides a patient interface comprising a patient interface element for delivering a breathing gas to a user (i.e. a mask) and a forehead support. One of the forehead support and the patient interface element comprises a shaft and the other of the forehead support and the patient interface element comprises a hollow tube in which the shaft is received, with the shaft slidable within the tube to permit adjustment of the position of the forehead support relative to the patient interface. One of the shaft and hollow tube are elastically deformable between configuration in which the shaft can be slid within the tube and a released configuration in which the sliding of the shaft within the tube is blocked.

This provides a simple to use adjustment mechanism with few components.

Figure 1:
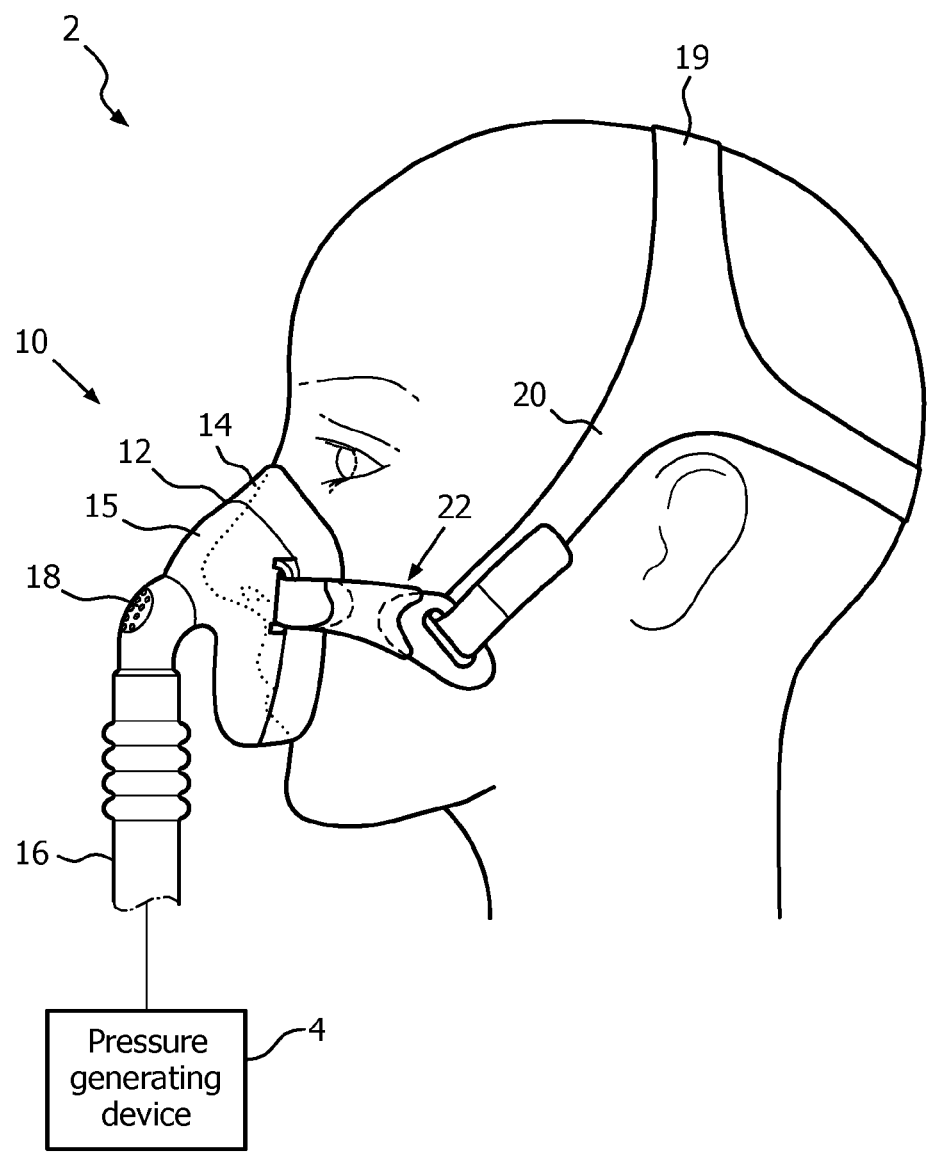
FIG. 1 shows a known patient interface.
Figure 2:
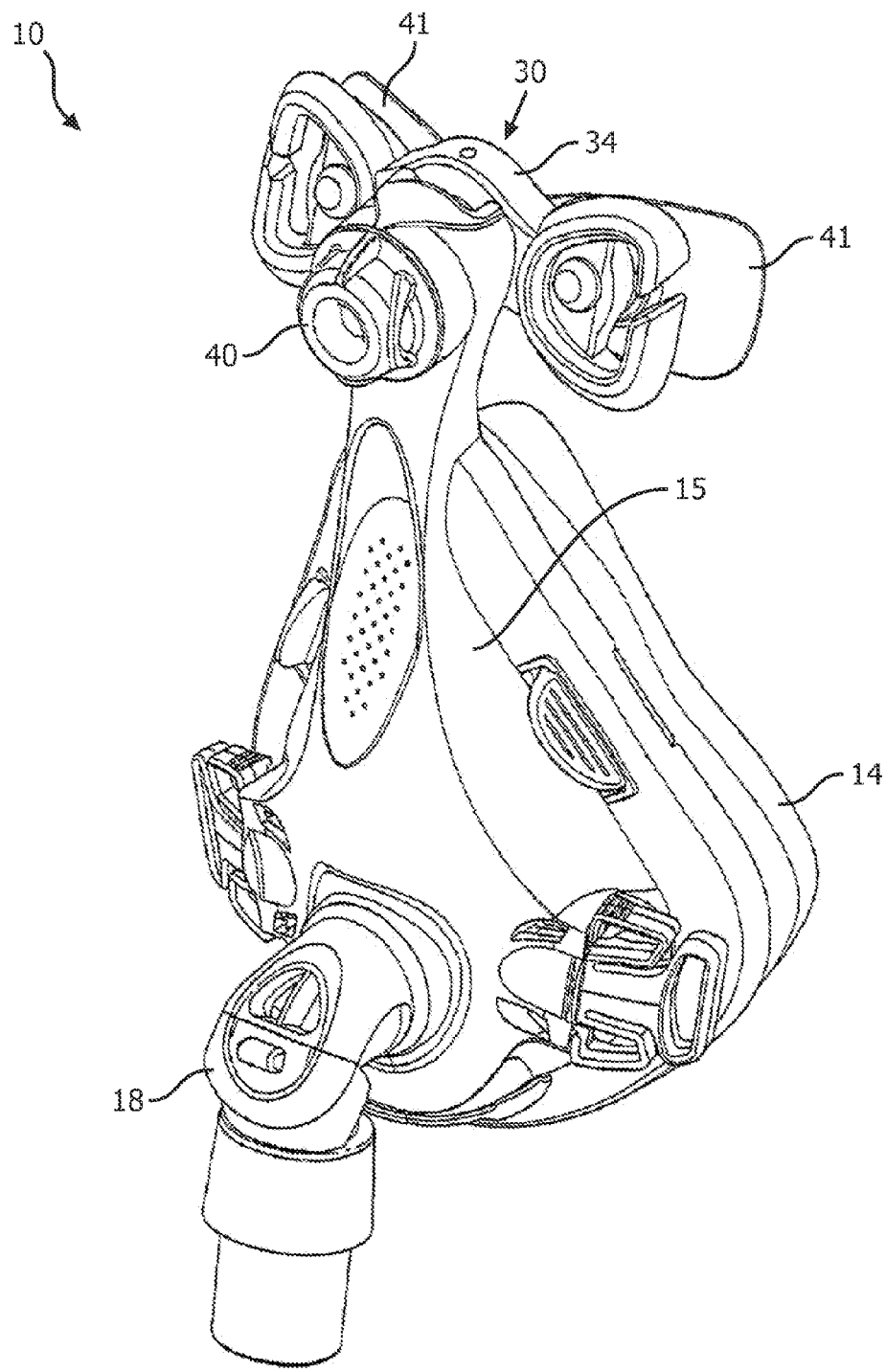
FIG. 2 shows a known patient interface as disclosed in US2010/0000542.

FIG. 2 is taken from US2010/0000542 and shows a patient interface assembly in the form of a full facial mask assembly 10 including a forehead support 30. The patient interface element (the mask part) is for delivering gas to the user and includes a frame 16, a cushion 14 adapted to form a seal with the patient's face, an elbow assembly 18 for connection to an air delivery tube (components 10,14,16,18 corresponding to those of the same number in FIG. 1).

FIG. 2 shows a forehead support 30 for reducing the forces on the patient's face, and including a frame 34 which carries forehead support cushions 41. In this example, the position of the forehead support is adjustable by a rotary knob 40.

The rotary knob comprises a screw-type actuator which moves the forehead support 30 along a generally linear path. The rotary adjustment knob 40 includes a threaded shaft, and the forehead support frame 34 includes an internally threaded tube.

When the adjustment knob 40 is rotated, the internally threaded tube of the forehead support 34 extends or retracts from the threaded shaft of the adjustment knob 40, which causes adjustable movement of the forehead cushions 41.

Figure 3:
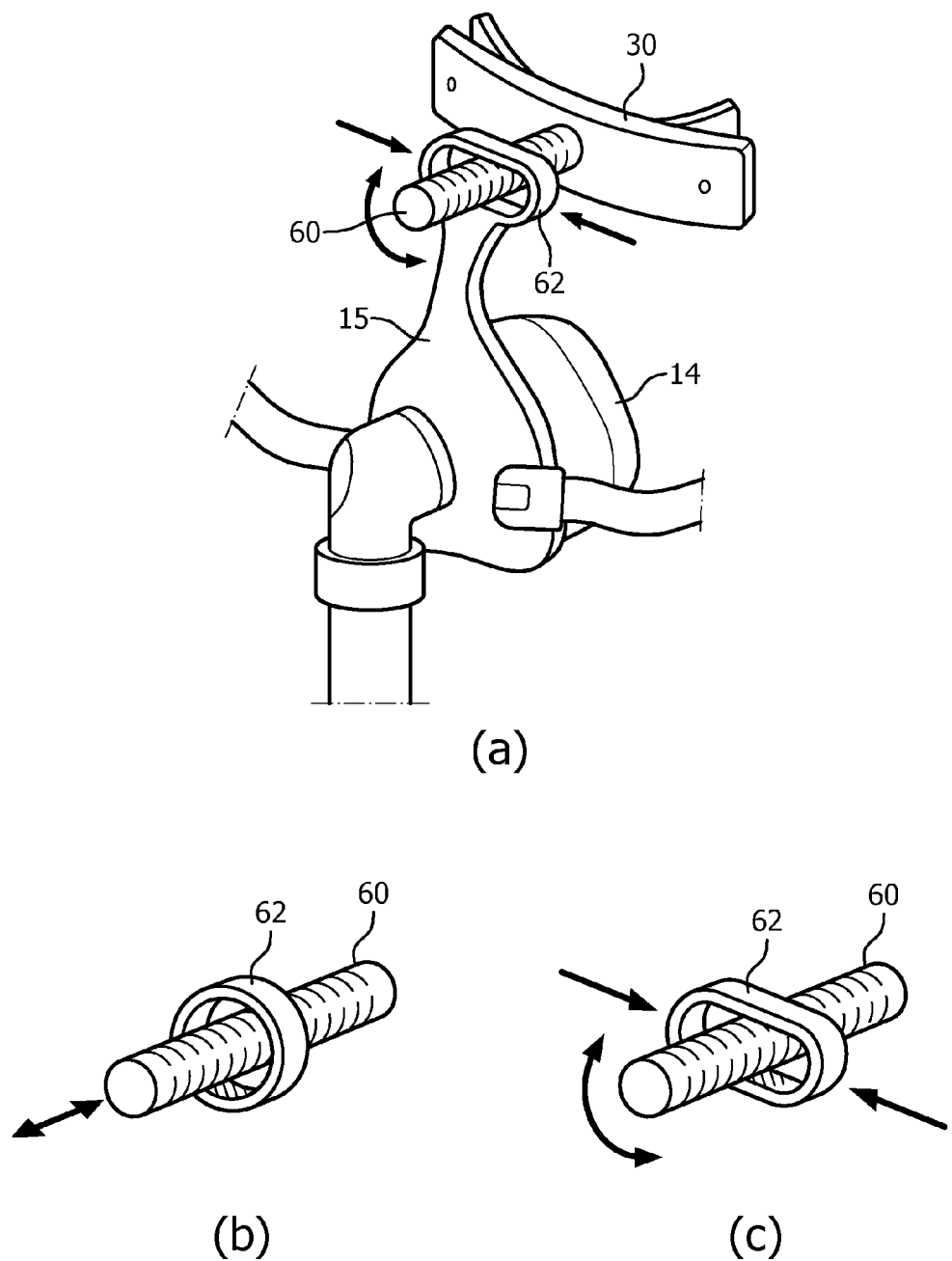
FIG. 3 shows a first example of patient interface of the invention.

FIG. 3 shows a first example of patient interface 10 of the invention, similar in structure to the design of FIG. 2, with a cushion 14 and shell 15 and a forehead support 30.

FIG. 3a shows the device in perspective view, FIG. 3b is used to explain the sliding configuration and FIG. 3c is used to explain the locked configuration.

This example uses a threaded shaft 60, and a hollow tube 62 is threaded. The hollow tube is normally oval, and the narrow dimension corresponds to the threaded shaft diameter. This means that even though the hollow tube does not contact the shaft all around its circumference, threaded adjustment is possible. This threaded adjustment is used for fine control only.

The hollow tube only needs to be long enough to grip the shaft, and no so long that the elastic deformation (described below) becomes difficult to implement.

The arrangement is shown only schematically in FIG. 3.

In one example, relative rotation between the forehead support 30 and the mask shell 15 is prevented, so that rotation of the shaft 60 (to provide the fine adjustment of position) results in linear movement of the forehead support (in the same way as in the device of FIG. 2). Thus, the shaft 60 can rotate relative to the forehead support 30. In another example, the shaft 60 is fixed to the forehead support, so that the fine adjustments comprise an integer number of 180 degree turns of the forehead support and shaft 60, since the forehead support should remain horizontal in its adjusted position.

There is also a rapid linear adjustment mode as shown in FIG. 3b. The tube 62 is elastically deformable between the oval shape in a released configuration and a circular shape in a deformed configuration with clearance around the shaft 60 as shown.

In this way, the shaft and attached forehead support can be slid in and out to a desired position. Releasing the elastic tube provides gripping at the selected position.

Thus, the user can rotate the shaft using a handle at the end of the shaft to reduce the distance to the forehead support with small incremental steps. Large steps can be made by pressing the tube, which is thus in the form of a flexible nut, and linearly pulling or pushing the handle.

As explained above, in one example, when the shaft 60 is rotated, this does not entrain rotation of the forehead support 30. For example a rotational coupling can be provided between the shaft 60 and the forehead support, so that shaft 60 is connected to the forehead support 30 but can still rotate relative to it. Relative rotation between the forehead support and the mask shell is prevented, for example by a guide and channel arrangement, or a pin and slot arrangement which couple the forehead support and mask shell together.

The flexible nut can be connected to the mask shell 15 such that it can be deformed as required, but does not rotated. For the large adjustments, the flexible nut is squeezed and the shaft is be moved. The forehead support can even be removed easily and replaced.

In this example the hollow tube is elastically deformable between a deformed configuration in which the shaft can be slid within the tube and a released configuration in which the sliding of the shaft within the tube is blocked.

Figure 4:
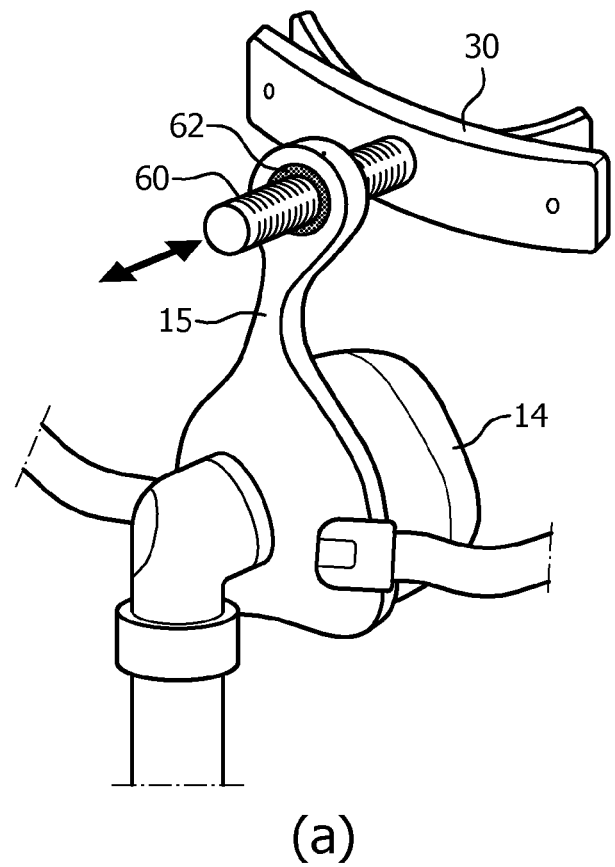
FIG. 4 shows a second example of patient interface of the invention.
Figure 4:
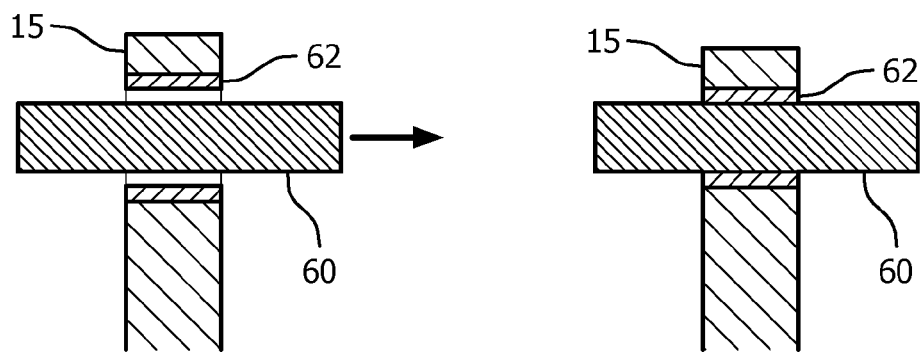

FIG. 4 shows a second example of patient interface 10 of the invention, similar in structure to the design of FIG. 2, with a cushion 14 and shell 15 and a forehead support 30. In this example, it is the shaft that is elastically deformable between a deformed configuration in which the shaft can be slid within the tube and a released configuration in which the sliding of the shaft within the tube is blocked.

FIG. 4a shows the device in perspective view, FIG. 4b is used to explain the sliding configuration and FIG. 4c is used to explain the locked configuration.

The shaft 60 in this case comprises a rubber rod which is connected to the forehead support 30. The rod 60 goes through a rubber ring 62 which is positioned in the mask shell 15. The shaft 60 is flexible, this is an advantage when the user is asleep and moves during sleep and part of the system interacts with a pillow.

The mask shell 15 and the cushions can stay at the same position on the face while the forehead support part can move. When the user wants to adjust the forehead support 30 he can pull on the shaft 60. The shaft 60 becomes thinner and longer and can move through the rubber ring 62 as shown in FIG. 4b. In the relaxed state shown in FIG. 4c, the shaft is gripped by the ring 62 to lock the forehead support in its linear adjustment position.

Other variations to the disclosed embodiments can be understood and effected by those skilled in the art in practicing the claimed invention, from a study of the drawings, the disclosure, and the appended claims. In the claims, the word "comprising" does not exclude other elements or steps, and the indefinite article "a" or "an" does not exclude a plurality. A single processor or other unit may fulfill the functions of several items recited in the claims. The mere fact that certain measures are recited in mutually different dependent claims does not indicate that a combination of these measured cannot be used to advantage. Any reference signs in the claims should not be construed as limiting the scope.

The invention claimed is:

1. A patient interface comprising:
a patient interface element for delivering a breathing gas to a user; and
a forehead support coupled to the patient interface element;
wherein one of the forehead support and the patient interface element comprises a shaft and the other of the forehead support and the patient interface element comprises a hollow tube in which the shaft is received, with the shaft slidable within the tube to permit adjustment of the position of the forehead support relative to the patient interface element,
wherein the shaft is elastically deformable between a stretched configuration in which the shaft can be slid within the tube and an un-stretched configuration in which the sliding of the shaft within the tube is blocked,
wherein the shaft is thinner and longer in the stretched configuration as opposed to the un-stretched configuration, and
wherein the hollow tube has an internal surface which grips the shaft when the shaft is in the un-stretched configuration.

2. A device as claimed in claim 1, wherein the shaft is coupled to the forehead support and the hollow tube is coupled to the patient interface element.

3. A patient interface assembly comprising a patient interface as claimed in claim 1, and headgear for holding the patient interface element and forehead support against the head of the patient.

4. A patient interface comprising:
a patient interface element for delivering a breathing gas to a user; and
a forehead support coupled to the patient interface element;
wherein one of the forehead support and the patient interface element comprises a shaft and the other of the forehead support and the patient interface element comprises a hollow tube in which the shaft is received, with the shaft slidable within the tube to permit adjustment of the position of the forehead support relative to the patient interface element,
wherein one of the shaft and hollow tube is elastically deformable between a deformed configuration in which the shaft can be slid within the tube and a released configuration in which the sliding of the shaft within the tube is blocked, and
wherein the shaft is threaded, and the hollow tube is threaded, and the threads engage in the released configuration, and wherein the tube is elastically deformable between an oval shape in the released configuration and a circular shape in the deformed configuration with clearance around the shaft.

5. A device as claimed in claim 4, wherein the hollow tube comprises an oval nut.

6. A device as claimed in claim 5, wherein the shaft is coupled to the forehead support and the hollow tube is coupled to the patient interface element.

7. A patient interface assembly comprising a patient interface as claimed in claim 6, and headgear for holding the patient interface element and forehead support against the head of the patient.

* * * * *